US006323357B1

(12) United States Patent
Kalchauer et al.

(10) Patent No.: US 6,323,357 B1
(45) Date of Patent: Nov. 27, 2001

(54) PROCESS FOR THE DIRECT SYNTHESIS OF ORGANOCHLOROSILANES USING RECOVERED CUCL CATALYST

(75) Inventors: Wilfried Kalchauer, Burghausen; Herbert Straussberger; Willibald Streckel, both of Mehring/Öd; Ulrich Goetze, Burghausen, all of (DE)

(73) Assignee: Wacker-Chemie GmbH, Munich (DE)

( * ) Notice: Subject to any disclaimer, the term of this patent is extended or adjusted under 35 U.S.C. 154(b) by 0 days.

(21) Appl. No.: 09/814,193

(22) Filed: Mar. 21, 2001

(30) Foreign Application Priority Data

Apr. 6, 2000 (DE) .............................................. 100 17 153

(51) Int. Cl.$^7$ ....................................................... C07F 7/16
(52) U.S. Cl. ............................................................ 556/472
(58) Field of Search ................................................ 556/472

(56) References Cited

U.S. PATENT DOCUMENTS

| | | |
|---|---|---|
| 4,758,352 | 7/1988 | Feldner et al. . |
| 5,306,328 | 4/1994 | Streckel et al. . |
| 5,530,151 * | 6/1996 | Tatterson et al. .................... 556/472 |
| 6,211,394 * | 4/2001 | Kalchauer et al. .................. 556/472 |

FOREIGN PATENT DOCUMENTS

| | | |
|---|---|---|
| 901 889 | 1/1954 | (DE) . |
| 42 05 980 A1 | 9/1993 | (DE) . |
| 0 210 418 B1 | 2/1987 | (EP) . |
| 0 550 857 A1 | 7/1993 | (EP) . |
| 0 682 032 A2 | 11/1995 | (EP) . |

OTHER PUBLICATIONS

Ullmann's Encyclopedia of Industrial Chemistry, 5$^{th}$ Edition, vol. A7, p. 574, 1965.
Derwent Abstract Corresponding To DE 901 889 [AN 1959:19662 CAPLUS], 1959.
Derwent Abstract Corresponding To EP 0 682 032 [AN 1995–394047 WPIDS], 1995.
Derwent Abstract Corresponding To DE 42 05 980 [AN 1993–281443 WPIDS], 1993.
Database Chemabs, Chem. Abstracts Service, Columbus, Ohio, AN 129:220485/XP 002166036, 1992.
International Search Report–mailed Jul. 17, 2001, 2001.

* cited by examiner

*Primary Examiner*—Paul F. Shaver
(74) *Attorney, Agent, or Firm*—Brooks & Kushman P.C.

(57) ABSTRACT

A process for the direct synthesis of organochlorosilanes using CuCl prepared from the copper-containing residues from the direct synthesis of organochlorosilanes, where, in the preparation of the CuCl, in a first step, copper from an aqueous suspension of the copper-containing residues is oxidized to $CuCl_2$ using mineral acid and oxidant, where mineral acid or oxidant or mineral acid and oxidant contain chlorine, giving an aqueous $CuCl_2$ solution, and in a second step, the aqueous $CuCl_2$ solution is reduced to CuCl using elemental iron.

18 Claims, No Drawings

PROCESS FOR THE DIRECT SYNTHESIS OF ORGANOCHLOROSILANES USING RECOVERED CUCL CATALYST

BACKGROUND OF THE INVENTION

1. Field of the Invention

The invention relates to a process for the direct synthesis of organochlorosilanes using CuCl prepared from the copper-containing residues from the direct synthesis of organochlorosilanes.

2. Background Art

In the so-called "direct synthesis" of organochlorosilanes, in particular methylchlorosilanies, metallic silicon is reacted with chloromethane in the presence of copper catalysts, optionally in the presence of further cocatalysts and promoters. When the direct synthesis is performed industrially in fluidized-bed reactors, fine fractions of silicon and copper catalyst, contaminated by carbon particles and by various metal compounds from the secondary constituents derived from the technical-grade silicon raw material, are discharged together with the crude silane reaction product and unreacted chloromethane, and separated therefrom by downstream separation units, for example, cyclones. Furthermore, a reactor residue comprising silicon, catalyst, and metal halides is formed, and is discharged continuously or batchwise from the fluidized-bed reactors. Drying and filtration processes also result in the formation of contaminated fine dusts.

Processes for the recovery of the copper from reactor residue and fine dusts are known. For example, U.S. Pat. No. 5,306,328 discloses that the copper content of residues from the synthesis of methylchlorosilane can be converted into soluble copper(II) salts. These copper(II) salts can be reduced to copper metal using iron powder. The disadvantage of this process is that iron and copper must be employed at least in a molar ratio of 1:1, and that if copper is not employed as a catalyst in metallic form, further processing is necessary.

Processes for the preparation of CuCl from aqueous solutions are known. In these processes, pure Cu(II) compounds or so-called "metallic waste copper" are preferably used as sources of copper, and dissolved in mineral acids such as hydrochloric acid. Hydrochloric acid-containing $CuCl_2$ solutions formed in etching processes for the production of circuit boards are also used. Solutions of this type, compared with the solutions produced in aqueous work-up of the process residues from the direct synthesis, have a relatively low content of additional impurities, for example, metal chlorides. After filtration, the copper-containing solutions are reduced to Cu(I) compounds with the aid of a suitable reducing agent, such as, for example, Cu, Fe, Zn, Al, hydroxylamine, sulfurous acid or $SO_2$. During this process, it is ensured that the CuCl formed remains in dissolved form through addition of complexing agents such as NaCl and/or hydrochloric acid. After re-filtration, the solubility is then reduced to below the limit for CuCl by suitable measures, so that the solid CuCl at least partially precipitates. This can be achieved, for example, by diluting the solution massively with water. The solid CuCl is separated by filtration, washed, and dried. This process is described, for example, in Ullmann's Encyclopedia of Industrial Chemistry, Volume A7, page 574.

The disadvantages of the foregoing process are that, first, due to the heavy dilution, relatively large reaction volumes and amounts of water are necessary, second, the resulting filtrates have to be worked up or suitably disposed; third, that an additional filtration step is necessary; and finally, relatively pure Cu(II) solutions are required as starting materials.

DE 901889 discloses that copper(I) chloride can be prepared in a yield of 85–90% from a copper(II) chloride solution with the aid of a reducing agent such as sulfur dioxide, sodium bisulfite or sodium sulfite. U.S. Pat. No. 4,758,352 discloses that the copper(I) chloride in the process described in DE 901889 is not separated quantitatively. The reason for the non-quantitative separation is given in Ullmann's Encyclopedia of Industrial Chemistry, 5th Edition, Volume A7, page 574, in which it is shown that with increasing chloride ion concentration in the solution, the solubility of CuCl likewise increases considerably.

SUMMARY OF THE INVENTION

The object of the present invention is to provide a process by means of which CuCl useful as an effective catalyst in the direct synthesis of organochlorosilanes can be prepared in a simple manner and in high yields from the copper-containing residues from the direct synthesis of organochlorosilanes.

DETAILED DESCRIPTION OF THE PREFERRED EMBODIMENT(S)

The present invention pertains to a process for the direct synthesis of organochlorosilanes using a CuCl catalyst component prepared from the copper-containing residues from the direct synthesis of organochlorosilanes, where, in the preparation of the CuCl catalyst, in a first step, copper from an aqueous suspension of the copper-containing residues from a direct process organochlorosilane synthesis is oxidized to $CuCl_2$ using mineral acid and oxidant, where the mineral acid, the oxidant or both the mineral acid and the oxidant contain chlorine, thereby providing an aqueous $CuCl_2$ solution, and in a second step, this aqueous $CuCl_2$ solution is reduced to CuCl using elemental iron.

The process is distinguished by the fact that CuCl can surprisingly be prepared in high yield and adequate purity from relatively highly contaminated $CuCl_2$ solutions without the disadvantages disclosed by the prior art arising. The recovered CuCl can be employed as an effective catalyst in the direct synthesis of organochlorosilanes. Compared with Cu oxide-based catalysts and copper metal catalysts, use of CuCl catalysts in the direct synthesis has the advantage that the reaction is initiated more quickly, that a smaller amount of catalyst is required for comparable reactivity, and that the reactivity of the catalyst is higher than a comparable amount of copper oxide-derived or metallic copper-containing catalyst based on metallic copper.

The isolation of the copper salt solution in the first step from process residues from the synthesis of organochlorosilanes, in particular methylchlorosilane, is described, for example, in U.S. Pat. No. 5,306,328, incorporated herein by reference. The process residues are, in particular, solid residues which preferably contain less than 1% by weight of silanes.

In a first step, the process residues are preferably suspended in acidic washing solutions produced in the work-up process. A mineral acid, preferably hydrochloric acid or sulfuric acid, is then added, and the suspension is treated with an oxidant, preferably oxygen, chlorine, NaOCl or $H_2O_2$. At least one of the two components comprising the mineral acid and the oxidant must contain chlorine or chloride. During this operation, all metal salts which usually occur in process residues in the synthesis of methylchlorosilane and some of the metals contained therein go into solution, while silicon and both the majority of the silicides, for example, iron disilicide, and carbon, remain undissolved. Particular preference is given to the recovery of copper(II) chloride using hydrochloric acid and oxygen. The oxygen can be supplied as atmospheric oxygen, as the pure gas, as oxygen enriched air, or as oxygen admixed with any non-interfering gas, i.e. nitrogen.

In order to separate accompanying insoluble substances such as fine carbon particles and silicon particles, the copper-salt solution is preferably filtered before further processing. It is possible to add auxiliaries such as flocculants, antifoams and filter aids to the copper-salt solution. After washing, the filter cake is substantially free from elutable toxic metal compounds and can either be sent to a sanitary landfill or employed as a raw material or aggregate in other processes, for example, as an aggregate for mineral building materials. The wash solutions can be re-employed for suspending the process residues.

In a second step, the aqueous $CuCl_2$ solution is reacted with elemental iron, preferably with agitation. Iron powder having a mean particle size in the range of 0.1 to 300 μm is preferred, since the high surface area increases the reaction rate. In this second step, the $CuCl_2$ solution may be added to the iron powder, or the iron powder may be added to the $CuCl_2$ solution.

The pH of the aqueous suspension obtained in the second step should preferably be adjusted by means of hydrochloric acid in such a way that the impurities introduced with the $CuCl_2$ solution do not precipitate out as hydroxides. At the same time, in the preferred embodiment, the highest possible pH should be targeted in order to minimize the solubility of the CuCl in the aqueous phase. The best results are generally obtained when the pH of the suspension is from 1.5 to 2.8. If the pH is too low, the rate of the undesired side reaction of iron and hydrochloric acid to produce iron chloride and hydrogen may increase excessively.

The temperature for the reaction in the second step is preferably in the range from 10° C. to 90° C., since this requires the least complex equipment. Temperatures in the range from 30° C. to 80° C. are particularly preferred.

The weight ratio between $CuCl_2$ solution and iron powder is preferably selected in such manner that after the reaction, virtually no Cu(II) is present in the aqueous phase and virtually no iron powder is present in the solid phase.

The second step, in particular, can be carried out under a protective gas, such as, for example, nitrogen or argon. The use of a protective gas is not necessary if it is ensured that significant amounts of atmospheric oxygen are not continuously introduced into the solution by excessively vigorous stirring.

The solid CuCl precipitates and is separated from the mother liquor of the second step. Separation can be carried out by any convenient method, for example by filtration. The CuCl can subsequently be washed with water and/or alcohol, sulfurous acid, glacial acetic acid or ether, but this is not absolutely necessary. The CuCl is subsequently dried, preferably in the absence of air/oxygen, such as, for example, under an inert gas or in vacuo. The aqueous solution after reaction with iron in the second step still contains, depending on the selected reaction conditions, from about 1 to 20 g of $Cu^+$ ions/l and a small proportion of Cu(II) ions.

The filtrate from the second step, in addition to Cu(I) and Cu(II) ions, comprises principally iron chloride and iron ions. The residual content of Cu ions in the filtrate from the second step is preferably reduced to elemental copper in a third step using elemental metal which is below copper in the electrochemical series of the elements. Suitable elemental metals are, in particular, zinc, aluminum and, in particular, iron. The elemental copper obtained in this way is preferably introduced into the second step and comproportionated therein with $CuCl_2$ to give CuCl. This enables the copper to be recovered with virtually no loss. If the reducing agent used in the third step is iron, the filtrate obtained can be used in waste-water treatment.

A principle advantage of the present invention is that an accumulation of impurities originating from process residues in the synthesis of organochlorosilane is not possible since these are removed in the filtrate obtained from the second and/or the third step.

In the organochlorosilane synthesis, the use of the process according to the invention enables virtually all the copper employed as catalyst to be recovered, with the advantage that copper is produced as a very reactive CuCl catalyst without additional processing steps. The "copper circuit" is substantially closed. Small losses of copper which are unavoidable in the organochlorosilane synthesis can be compensated for by introducing metallic copper, copper compounds or aqueous copper solutions into the process steps, there being no need to make high demands on the purity of these substances.

In the following examples, unless otherwise stated, all amounts are based on the weight, all pressures are 0.10 MPa (abs.), and all temperatures are 20° C.

EXAMPLE 1

Example of a first step involving preparation of a $CuCl_2$ solution from process residues from the synthesis of methylchlorosilane:

400 g of a mixture of reactor residues, cyclone dust and dryer dust from crude silane filtration were introduced with stirring into 1000 ml of wash water from Cu leaching (see end of Example 1). The process of suspending the mixture was carried out under nitrogen as inert gas, since the process residues can be pyrophoric. Air (about 300 l/h) was subsequently passed into this suspension at about 50° C. with the aid of a gas inlet tube, and the pH in the suspension was held in the range of 1 to 3 by continuous addition of 20% strength hydrochloric acid. After a leaching time of 5 hours, a pH of 1.7 was reached using 20% strength hydrochloric acid, the solution was filtered, and the solid residue was washed with 1000 ml of water. An eluate experiment on the moist residue in accordance with DIN 38414 gave 0.008 g/l of elutable copper.

The following concentrations of metal ions were measured in the filtrate obtained:

| | |
|---|---|
| Copper | 61.5 g/l |
| Aluminum | 3.9 g/l |
| Calcium | 0.6 g/l |
| Iron | 2.0 g/l |
| Magnesium | 0.3 g/l. |

Standardized to the same Cu concentration, the following concentrations were measured for comparison to a "waste acid" from the production of circuit boards:

| | |
|---|---|
| Aluminum | 0.007 g/l |
| Calcium | 0.002 g/l |
| Iron | 0.016 g/l. |

EXAMPLE 2

Example of a second step involving preparation of CuCl by reaction with iron, and third step, involving preparation of CuCl by comproportionation of copper metal recovered from the filtrate in the second step.

1000 ml of water, 16 g of moist copper having a water content of 20%—prepared from an iron cementation from the filtrate from CuCl preparation formed from the present Example, and 48 g of iron powder having a mean particle size of from 60 to 70 μm, were introduced into a stirred vessel and warmed to 50° C. 1500 ml of a copper(II) chloride solution prepared in accordance with Example 1 were added over the course of 20 minutes, under nitrogen as inert gas. The mixture was subsequently stirred for a further 60 minutes, cooled to room temperature and adjusted to pH 1.9 by means of 20% strength hydrochloric acid. The solid CuCl formed was separated from the iron chloride solution via a suction filter under nitrogen as protective gas. After washing with 150 ml of water with aspiration, the CuCl thus obtained was dried at 80° C. under reduced pressure. The filtrate and wash water were combined. The total concentration of Cu ions was determined by ICP, and was 4.8 g/l. 20 g of iron powder were stirred into this solution. After a post-stirring time of 45 minutes and adjustment of the pH to 1.9, the deposited metallic copper was subsequently separated by filtration. Obtained was 16 g of moist material having a water content of 20%. A total copper concentration of less than 0.05 g/l was measured in the iron chloride solution.

The following elemental analytical data were determined by elemental analysis of the CuCl:

| | |
|---|---|
| Copper | 63.2% |
| Aluminum | 0.08% |
| Calcium | 0.02% |
| Iron | 0.30% |
| Magnesium | 0.01%. |

EXAMPLES 3 AND 4

These examples pertain to the synthesis of methylchlorosilane using copper catalysts.

The experimental synthesis plant comprises a laboratory fluidized-bed reactor consisting of a vertical glass tube having an internal diameter of 25 mm, a height of 500 mm surrounded by a heating coil, a sintered bubbler, and a distillation bridge with brine cooling and associated receiving flask. The procedure may be described as follows:

Copper catalyst, as stated in Table 1, 1 g of zinc oxide, 8 mg of tin powder and 120 g of silicon powder having a particle size of 70 to 250 μm, were mixed intimately, introduced into the reactor, and heated to 340° C. under a 40 l/h stream of nitrogen. 40 l/h of chloromethane were subsequently passed through the reactor, and the catalyst material was heated to 395° C. After an induction period, silane formation commenced, the reaction temperature was reduced to 360° C., and 50 ml of a mixture of methylchlorosilanes were collected (start phase). A further 30 ml of methylchlorosilanes were subsequently collected. The time taken for these 30 ml of silanes to form is referred to as the production phase, the production rate (PR2) being calculated from the formula PR2=mg of methylchlorosilanes in the production phase divided by the surface area of the silicon×minutes in the production phase.

The silane composition of the 30 ml of methylchlorosilane collected in the production phase is determined in % by weight by means of GC analysis:

TABLE 1

| Example | Cu catalyst | Induction time | PR2 | Dimethyldichlorosilane |
|---|---|---|---|---|
| 3 | 6.0 g CuO | 27 minutes | 58 | 84.9% |
| 4 | 7.3 g CuCl | 4 minutes | 125 | 87.9% |

The CuO catalyst from Example 3 was prepared by the process described in U.S. Pat. No. 5,306,328, Example 5. Based on the Cu content, 6.0 g of CuO correspond to 7.3 g of CuCl catalyst.

Example 4 indicates that a) the induction time for the catalyst prepared in accordance with the invention is shorter than for the catalysts prepared in accordance with U.S. Pat. No. 5,306,328, and b) for the same amount of copper catalyst, based on metallic copper, CuCl gives higher reactivity.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for the direct synthesis of organochlorosilanes employing a catalyst comprising CuCl as a catalyst component, wherein at least a portion of said CuCl is recycled CuCl prepared from the copper-containing residues from the direct synthesis of organochlorosilanes, wherein the preparation of the recycled CuCl comprises, in a first step, oxidizing copper from an aqueous suspension of the copper-containing residues from a direct organochlorosilane synthesis to $CuCl_2$ using mineral acid and oxidant, wherein said mineral acid, said oxidant, or said mineral acid and said oxidant contain chlorine, thus providing an aqueous $CuCl_2$ solution, and in a second step, reducing said aqueous $CuCl_2$ solution to CuCl using elemental iron.

2. The process of claim 1, wherein the mineral acid employed in the first step is hydrochloric acid or sulfuric acid.

3. The process of claim 1, wherein the oxidant employed in the first step is selected from the group consisting of oxygen, chlorine, NaOCl and $H_2O_2$.

4. The process of claim 2, wherein the oxidant employed in the first step is selected from the group consisting of oxygen, chlorine, NaOCl and $H_2O_2$.

5. The process of claim 1 in which $CuCl_2$ remaining in a filtrate from the second step is reduced to elemental copper in a third step using an elemental metal which is beneath copper in the electrochemical series of the elements.

6. A process as claimed in claim 5, in which the elemental metal employed in the third step is iron.

7. A process as claimed in claim 5 in which the elemental copper obtained in the third step is added in the second step and comproportionated therein using $CuCl_2$ to produce CuCl.

8. A process as claimed in claim 6 in which the elemental copper obtained in the third step is added in the second step and comproportionated therein using $CuCl_2$ to produce CuCl.

9. The process of claim 1, wherein at least a portion of the mineral acid and/or oxidant supplied in said first step is derived from a further step in said process.

10. The process of claim 2, wherein at least a portion of the mineral acid and/or oxidant supplied in said first step is derived from a further step in said process.

11. The process of claim 3, wherein at least a portion of the mineral acid and/or oxidant supplied in said first step is derived from a further step in said process.

12. The process of claim 4, wherein at least a portion of the acid and/or oxidant supplied in said first step is derived from a further step in said process.

13. The process of claim 5, wherein at least a portion of the mineral acid and/or oxidant supplied in said first step is derived from a further step in said process.

14. The process of claim 6, wherein at least a portion of the mineral acid and/or oxidant supplied in said first step is derived from a further step in said process.

15. The process of claim 7, wherein at least a portion of the mineral acid and/or oxidant supplied in said first step is derived from a further step in said process.

16. A process for the preparation of organochlorosilanes by the direct process employing a copper (I)-containing catalyst and optionally cocatalysts and promoters without substantial loss of copper during continuous operation or in successive batch or continuous campaigns, said process comprising a) introducing silicon metal, at least one chloroorganiic compound, and a catalyst comprising copper metal and optionally cocatalysts and/or promoters into a heated reactor;

b) recovering organochlorosilanes from said reactor and metal-containing solids containing zero-valent metals and metal compounds;

c) suspending said metal-containing compounds in a composition comprising mineral acid and an oxidant, at least one of said mineral composition or said oxidant containing chlorine, thus providing an aqueous copper (II) solution;

d) adding iron metal to said aqueous copper (II) solution at a pH of between 1 and 3 to obtain a solution containing Cu(I);

e) optionally filtering said solution containing Cu(I) to remove solids;

f) precipitating CuCl from said solution containing Cu(I), separating precipitated CuCl from the mother liquor containing said CuCl, drying said precipitated CuCl and adding at least a portion of said CuCl to a direct organochlorosilane process (a) as a copper catalyst;

g) adding a metal lower in the electromotive series than copper to said mother liquor of step f) to precipitate remaining copper as copper(O);

h) recycling said copper (O) by one or both of h1) introducing said copper (o) to a direct process reactor to supply at least a portion of said copper catalyst, or h2) introducing said copper (O) to step (C) and/or to step (d) and comproportionating with Cu(II) to form Cu(I).

17. The process of claim 16, wherein the pH of step d) is between 1.5 and 2.8.

18. The process of claim 16, wherein at least a portion of said mineral acid is obtained by recycle of mother liquor from step f).

* * * * *

UNITED STATES PATENT AND TRADEMARK OFFICE
CERTIFICATE OF CORRECTION

PATENT NO. : 6,323,357 B1
DATED : November 27, 2001
INVENTOR(S) : Wilifried Kalchauer et al.

It is certified that error appears in the above-identified patent and that said Letters Patent is hereby corrected as shown below:

Title page,
Item [54], Title, delete "CUCL" and insert therefore -- CuCl --.

Column 7,
Line 15, after "the" insert -- mineral --.

Signed and Sealed this

Twenty-fifth Day of June, 2002

Attest:

Attesting Officer

JAMES E. ROGAN
*Director of the United States Patent and Trademark Office*